United States Patent [19]
Singh et al.

[11] Patent Number: 5,106,706
[45] Date of Patent: Apr. 21, 1992

[54] OXIDE MODIFIED AIR ELECTRODE SURFACE FOR HIGH TEMPERATURE ELECTROCHEMICAL CELLS

[75] Inventors: Prabhakar Singh, Export; Roswell J. Ruka, Churchill Boro, Allegheny County, both of Pa.

[73] Assignee: Westinghouse Electric Corp., Pittsburgh, Pa.

[21] Appl. No.: 599,530

[22] Filed: Oct. 18, 1990

[51] Int. Cl.⁵ .............................................. H01M 8/10
[52] U.S. Cl. ...................................... 429/31; 429/33; 429/40
[58] Field of Search ...................... 429/30, 31, 33, 40

[56] References Cited

U.S. PATENT DOCUMENTS

| | | | |
|---|---|---|---|
| 4,490,444 | 12/1984 | Isenberg | 429/31 |
| 4,547,437 | 10/1985 | Isenberg et al. | 429/30 |
| 4,562,124 | 12/1985 | Ruka | 429/30 |
| 4,885,078 | 12/1989 | Spengler et al. | 204/432 |
| 4,894,297 | 1/1990 | Singh et al. | 429/31 |

OTHER PUBLICATIONS

Bergmann et al., *Extended Abstracts of Presentations at Workshop on High Temperature Solid Oxide Fuel Cells,* May 5-6, Brookhaven National Laboratory, "Transport Considerations in Oxygen Electrodes of the Triphase Boundary Type for Zirconia Cells".

*Primary Examiner*—Anthony Skapars
*Attorney, Agent, or Firm*—Daniel P. Cillo

[57] ABSTRACT

An electrochemical cell is made having a porous cermet electrode (16) and a porous lanthanum manganite electrode (14), with solid oxide electrolyte (15) between them, where the lanthanum manganite surface next to the electrolyte contains a thin discontinuous layer of high surface area cerium oxide and/or praseodymium oxide, preferably as discrete particles (30) in contact with the air electrode and electrolyte.

10 Claims, 3 Drawing Sheets

OXIDE MODIFIED AIR ELECTRODE SURFACE FOR HIGH TEMPERATURE ELECTROCHEMICAL CELLS

GOVERNMENT CONTRACT CLAUSE

The Government of the United States of America has rights in this invention pursuant to Contract No. DE-AC-21-80-ET17089, awarded by the United States Department of Energy.

BACKGROUND OF THE INVENTION

This invention relates to an air electrode having discrete, small, high surface area oxide particles on its exterior surface which serve as nucleating sites for subsequently applied solid electrolyte.

High temperature solid oxide fuel cell configurations are well known, and taught, for example, in U.S. Pat. No. 4,490,444 (Isenberg), herein incorporated by reference. There, a porous, calcia stabilized zirconia support tube, having a porous air electrode of, for example calcium, strontium, magnesium or zirconium oxide doped lanthanum manganite was taught, with an attached, axially elongated, narrow interconnection strip of calcium, strontium, or magnesium oxide doped lanthanum chromite. The air electrode was coated with a 20 micrometer to 50 micrometer thick, solid, non-porous, yttria stabilized zirconia electrolyte. A porous, nickel-zirconia cermet, exterior fuel electrode, about 50 micrometers thick, covered most of the electrolyte. In another embodiment, taught in U.S. Pat. No. 4,547,437 (Isenberg et al.), an electrode-protective, porous, continuous interlayer of calcium and cobalt doped yttrium chromite was disposed between the air electrode and the electrolyte. Also, Bergmann et al., in *Extended Abstracts Of Presentations At Workshop On High Temperature Solid Oxide Fuel Cells*, "Transport Considerations In Oxygen Electrodes Of The Triphase Boundary Type For Zirconia Cells" May 1977, Brookhaven National Laboratory, taught complete, continuous separation layers of ceria or doped zirconia between silver, platinum or indium oxide electrodes and zirconia electrolyte, in order to decrease polarization losses.

In U.S. Pat. No. 4,562,124 (Ruka), cerium was incorporated into the atomic structure of the air electrode to provide the composition of $La_{.3}Ca_{.5\ to\ .6}Ce_{.1\ to\ .2}MnO_3$. The addition of cerium helped match the coefficient of thermal expansion of the air electrode to the support tube and the electrolyte. For a variety of reasons, cerium compounds have also been applied to fuel electrodes of electrochemical cells, as an impregnated material, as in U.S. Pat. No. No. 4,894,297 (Singh et al.) and as an exterior particulate film, as in U.S. Pat. No. 4,885,078 (Spengler et al.)

In conventionally fabricated tubular fuel cells, electrolyte penetration within the air electrode and encapsulation of the air electrode surface by the electrolyte film has been observed near the air electrode-electrolyte interface. After electrical testing, the air electrode of these cells have been found to show structural changes in terms of porosity-formation and densification. Such undesirable structural changes taking place in the air electrode near the air electrode-electrolyte interface are postulated to be due to changes in the oxygen stoichiometry of the air electrode, resulting from the partial encapsulation of the air electrode particles at the air electrode-electrolyte interface. Partially encapsulated air electrode surfaces formed near the electrolyte-air electrode interface may also inhibit oxygen reduction reaction due to limiting the surface area for electron exchange at the interface, and allow oxygen loss from the air electrode lattice during cell operation at moderate-to-high current densities.

One of the main objects of this invention is to reduce oxygen loss from air electrode particles in contact with the electrolyte and increase the active area for the electron exchange reactions with oxygen at the electrode-electrolyte interface.

SUMMARY OF THE INVENTION

Accordingly, the present invention resides in an electrochemical cell comprising a porous cermet electrode and a porous lanthanum manganite electrode, with stabilized zirconia solid oxide electrolyte therebetween, characterized in that the lanthanum manganite electrode surface next to the electrolyte contains a porous, discontinuous layer of a material selected from the group consisting of cerium oxide praseodymium oxide and mixtures thereof, and where electrolyte contacts both the lanthanum manganite and the discontinuous oxide layer.

Preferably, the discontinuous layer of cerium oxide is in discrete particle form having diameters from approximately 0.01 micrometer to 0.1 micrometer, and has a high surface area of from approximately 35 $m^2$/gram to 150 $m^2$/gram, where from 90% to 100% of the particles are in the top 50 micrometers of the air electrode structure near the electrolyte. The preferred electrochemical cell is a tubular fuel cell.

The discontinuous layer of, for example, cerium oxide, prevents any encapsulation of or substantial penetration into the porous air electrode structure by the electrolyte, yet provides abundant nucleation sites for electrolyte formation and superior bonding to the air electrode surface. Cells made with this nucleating oxide layers have showed superior performance including lower voltage losses due to electrode polarization, and stability of the air electrode-electrolyte interface with minimal densification of the air electrode at the interface over long-term cell operation at 1,000° C.

BRIEF DESCRIPTION OF THE DRAWINGS

In order that the invention can be more clearly understood, convenient embodiments thereof will now be described, by way of example, with reference to the accompanying drawings in which.

DESCRIPTION OF THE PREFERRED EMBODIMENTS

Figure 1:
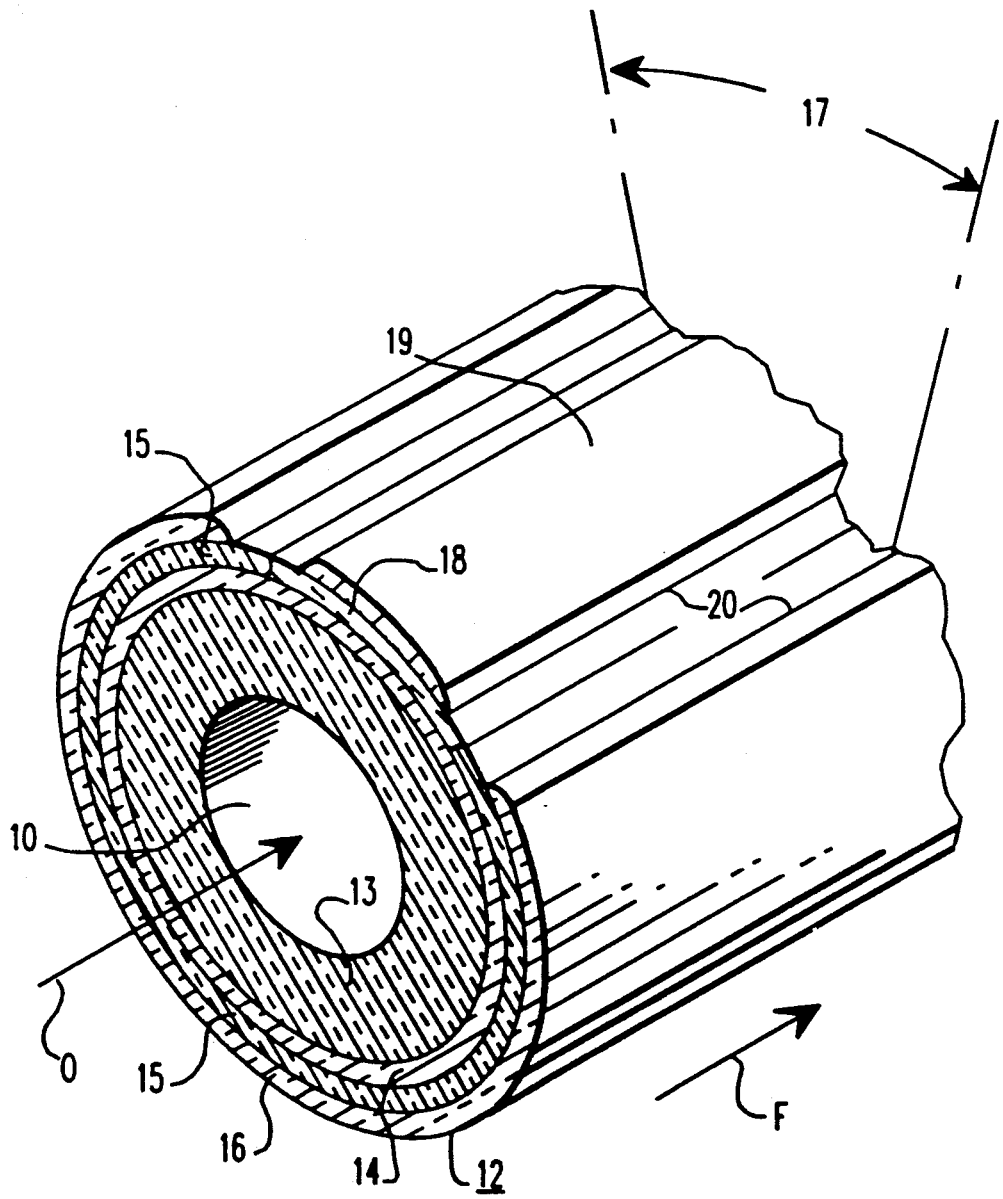
FIG. 1 is an isometric view in section of a preferred, tubular, solid oxide fuel cell which can be made according to this invention.

Referring now to FIG. 1 of the drawings, air or oxygen 0, flowing through the open interior 10 of electrochemical cell 12, for example, an operating high temperature fuel cell, permeates through optional porous support tube 13 comprising, for example, sintered calcia stabilized zirconia, to air electrode 14, where the oxygen is converted to oxygen ions at the surface of electrolyte 15. The oxygen ions are conducted through oxygen ion conducting electrolyte 15 to fuel electrode 16 where they react with fuel F, to generate electricity. Also shown in the drawing are: longitudinal space 17, containing an axially elongated interconnection 18 which extends down a narrow axial segment of the tube, for making electrical connections from the underlying air electrode to the fuel electrode of a cell tube (not shown) lying next to it and an electronically insulating gap 20. A metal or fuel electrode type of material 19 can be coated over interconnection 18. A plurality of these cells can be electrically connected together to provide a generator.

The air electrode 14, is a typically tube of porous, calcia or strontia, doped lanthanum manganite, to which zirconia is sometimes added, hereinafter "lanthanum manganite," usually formed by extrusion or a slurry dip-sinter operation. This layer is usually from 500 micrometers to 2,000 micrometers thick. Electrolyte 15 must be a solid material through which oxygen ions can diffuse or permeate. The electrolyte material is preferably an oxide having a fluorite structure or a mixed oxide in the perovskite family, but other simple oxides, mixed oxides, or mixtures of simple and mixed oxides can be used. The preferred electrolyte material is a stabilized zirconia based ceramic, a readily available commercial material. A useful composition is $(ZrO_2)_{0.90}(Y_2O_3)_{0.10}$ as that material works well in solid oxide fuel cells. The electrolyte 15 is applied over a substantial portion of the inner, air electrode 14, as shown in FIG. 1, next to the narrow radial segment interconnection 18, which is usually applied first so that the electrolyte can overlap it, as shown.

An outer, porous, cermet fuel electrode 16 is then deposited over a substantial portion of the electrolyte 15, as shown in FIG. 1. First, particles of an electronic conductor are applied to the electrolyte surface, then a skeleton of yttrium and zirconium oxide is grown around the particles by a modified electrochemical vapor deposition process. The preferred particles are nickel, cobalt, and alloys and mixtures thereof, as these metals are stable, sulfur resistant, and have an acceptable oxidation potential.

The electrolyte is applied to the top of the air electrode by a chemical/electrochemical vapor deposition process using two reactant gases. The first reactant used to form the electrolyte 15 is a source of oxygen such as water vapor, carbon dioxide, or oxygen itself, which is fed from the inside of the tube, through the optional support 13 and the inner, porous air electrode 14. The second reactant used to form the electrolyte are metal halides, which are fed to the outside of the air electrode 14. Chlorides are preferred as they are inexpensive and have acceptable vapor pressures. The reaction of the first and second reactants produces a metal oxide electrolyte material. Where the electrolyte 14 is stabilized zirconia, it will be necessary to use a mixture of a zirconium halide and a halide of the stabilizing element as the second reactant.

Figure 2:
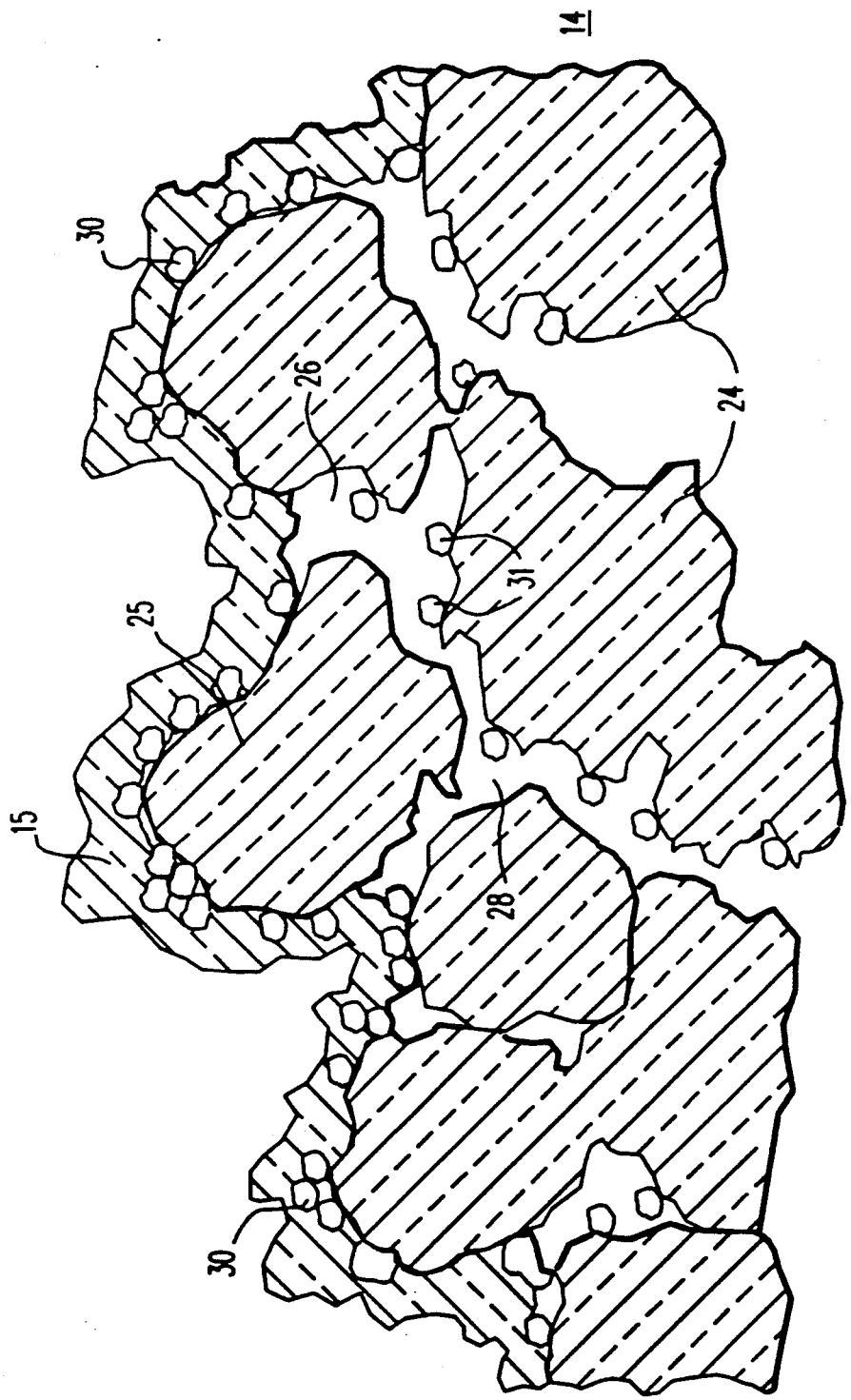
FIG. 2 which best shows the invention, is an idealized cross-section of the air electrode-electrolyte interface of the fuel cell of FIG. 1, showing the porous, discontinuous electrolyte nucleating layer of this invention, at the beginning of electrolyte deposition.

Referring now to FIG. 2, an idealized portion of the air electrode structure 14 is shown, with solid oxide electrolyte 15 just beginning to nucleate and grow over the air electrode top surface. Lanthanum manganite, usually in the form of sintered particles 24, about 12 micrometer to 15 micrometers in diameter, form an air electrode surface containing interconnecting pores or voids, such as 26 and 28. The term "particle diameter" as used herein will mean the length measurement of the particles, since the particles are rarely perfectly round. After complete deposition, the electrolyte layer 15 will be much thicker than shown, and will be non-porous. The air electrode surface next to the electrolyte contains a porous, thin, discontinuous layer of at least one of cerium oxide or praseodymium oxide, preferably as discrete, high surface area particles 30, which provide nucleating sites for subsequent electrolyte deposition. Exterior cermet fuel electrode (not shown) is applied after electrolyte formation.

These particles 30 have diameters of from approximately 0.01 micrometer to 0.1 micrometer, and so, are substantially smaller than the sintered lanthanum manganite particles 24. These particles are chemically stable in oxygen at 1,000° C., do not react with the air electrode material at 1,000° C., and are oxygen ion as well as electron conducting. These particles have high surface areas of from approximately 35 $m^2$/gram to 150 $m^2$/gram most preferably from 50 $m^2$/gram to 100 $m^2$/gram, providing a vast number of sites for nucleation and growth of electrolyte by contact of halide vapors with oxygen containing vapors by chemical vapor deposition, as described previously. Since these particles 30 are both electronic and ion-conducting, they also contribute to further electrolyte deposition by electrochemical vapor deposition as the non-porous electrolyte film continues to grow thicker with time. Preferably, the particles 30 are cerium oxide particles. Particles above or below the stated particle size range and surface area range will not provide as advantageous a number of nucleating sites and can allow particle plugging of the air electrode pores or excessive electrolyte impregnation into the air electrode.

As can be seen from FIG. 2, some cerium oxide or praseodymium oxide particles, such as particles 31 may be deposited within interior pores 26 or 28 of the air electrode structure, but preferably, from 90% to 100% of the particles will be in the top 50 micrometers of the air electrode structure, most preferably in the top 20 micrometers of the air electrode structure, near the electrolyte 15. The closer to the top of the air electrode the nucleating particles 30 are placed, the better chance the air electrode pores will remain interconnecting and free to easily pass oxygen containing gas from the interior of the air electrode to the electrolyte 15.

As can also be seen from FIG. 2, the electrolyte 15, while contacting both the lanthanum manganite particle 24 and the discontinuous layer of nucleating particles 30, does not encapsulate or substantially penetrate or enclose the air electrode structure. Thus, pores 26 and 28, for example, remain open. If electrolyte permeated too deeply into pores 26 and 28, air electrode particle 25, for example, would be surrounded and rendered useless as an interface site where oxygen containing gas contacts oxygen ion conducting electrolyte. The electrolyte 15, while not penetrating deeply into the air electrode structure 14, still is firmly bonded to the air electrode.

The discontinuous layer of particles 30 can be applied by any means, preferably by simple dusting with oxide powder, or a slurry dip-sinter operation. A variety of modified impregnation techniques may also be used so long as the oxide is formed primarily at the interface between the air electrode structure 14 and the electrolyte 15. The invention will now be illustrated by the following non-limiting Example.

EXAMPLE

Self-supported tubular fuel cells using $La_{.8}Ca_{.2}MnO_3$ air electrode material, yttria stabilized zirconia electrolyte, nickel-zirconia cermet fuel electrode and magnesia doped lanthanum chromite interconnect were made, using well-known fabricating techniques. On one cell, cell A, a porous, discontinuous layer of $CeO_2$ particles, prepared by hydroxide precipitation, having diameters of approximately 0.05 micrometer to 0.1 micrometer, and surface areas of approximately 65 $m^2$/gram, were deposited on the air electrode surface, to act as an electrolyte nucleating layer. The $CeO_2$ particles were deposited by rubbing onto the air electrode surface, and all the particles remained substantially on top of the air electrode surface. The electrolyte and fuel electrode were subsequently applied to the cells by standard chemical-electrochemical vapor deposition techniques described previously.

Figure 3:
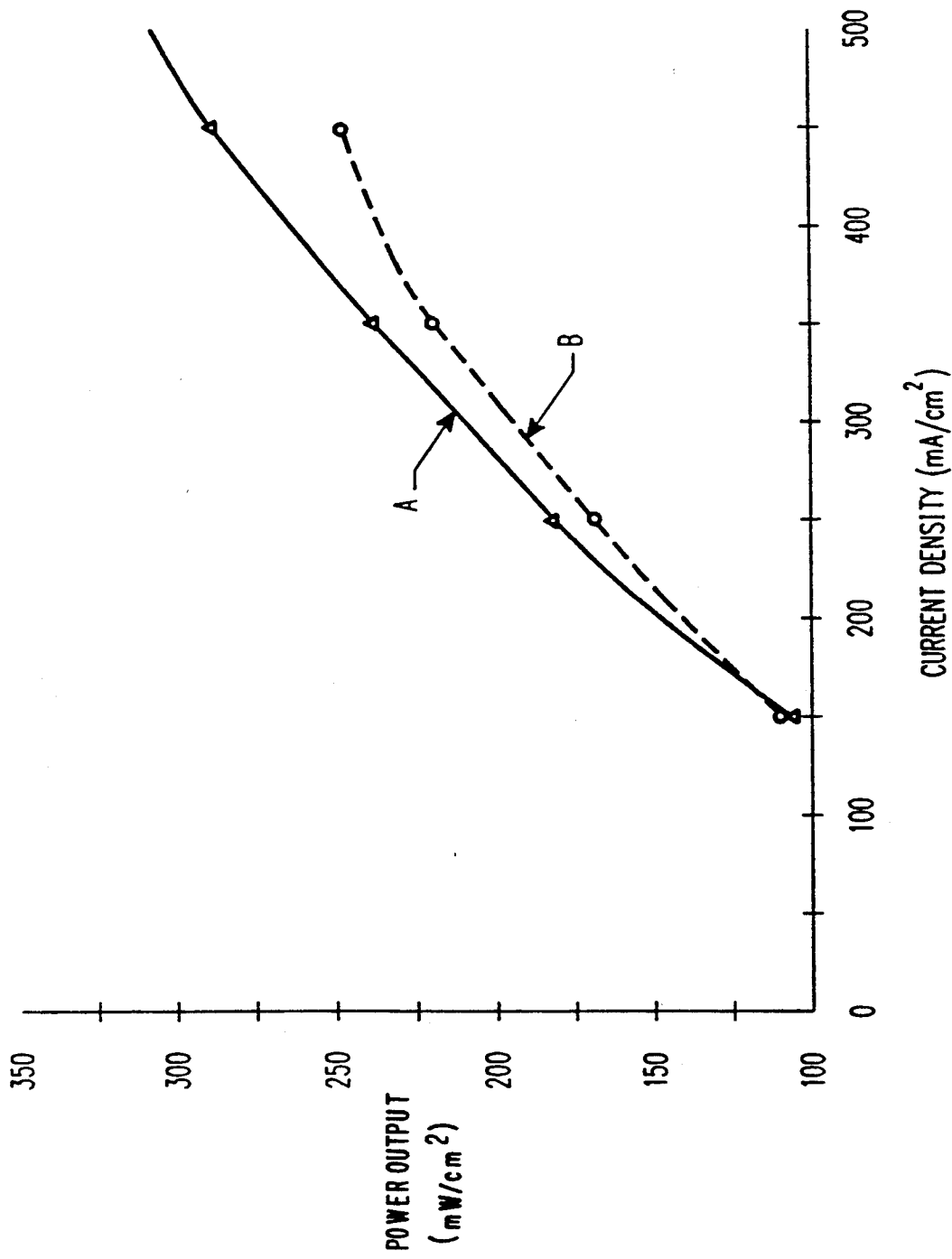
FIG. 3 is a graph of power output versus current density of a standard fuel cell and a fuel cell having the discontinuous, electrolyte nucleating layer of this invention.

Fabricated cells, one with the electrolyte nucleating layer, cell A, and the other without that layer, cell B, were then electrically tested at 1,000° C. in an 89% $H_2$-11% $H_2O$ fuel gas mixture with air as oxidant. Electrical characteristics were obtained and are shown in FIG. 3, as plots of power output in mW/$cm^2$ vs current density in mA/$cm^2$. From the data it is clear that cell A, represented by curve A, containing $CeO_2$ nucleating particles produced higher power, and also showed higher performance at higher current densities than cell B, represented by curve B, not containing $CeO_2$ particles. Cross-sectional micrographs of cell A, showed dense electrolyte tightly connected to the air electrode.

We claim:

1. An electrochemical cell comprising a porous cermet electrode and a porous lanthanum manganite electrode, with stabilized zirconia solid oxide electrolyte therebetween, where the lanthanum manganite electrode surface next to the electrolyte contains a porous, discontinuous layer of a material selected from the group consisting of cerium oxide, praseodymium oxide and mixtures thereof, and where the electrolyte contacts both the lanthanum manganite and the discontinuous oxide layer.

2. The cell of claim 1, where the cermet electrode is nickel-zirconia, the electrolyte is a zirconia based ceramic, and the lanthanum manganite is in the form of sintered particles having particle diameters from 1 micrometer to 15 micrometers.

3. The cell of claim 1, in tubular fuel cell configuration.

4. The cell of claim 1, where the air electrode is from 500 micrometers to 2,000 micrometers thick, the discontinuous layer is in the form of discrete particles having diameters from 0.01 micrometer to 0.1 micrometer, and where 90% to 100% of the particles are in the top 50 micrometers of the air electrode structure next to the electrolyte.

5. The cell of claim 1, where the discontinuous layer is in the form of discrete particles having a surface area of from approximately 35 $m^2$/gram to 150 $m^2$/gram.

6. The cell of claim 1, where the discontinuous layer consists of cerium oxide particles, said particles being effective to provide nucleating sites for electrolyte formation.

7. A plurality of the cells of claim 1, electrically connected together.

8. A tubular fuel cell comprising a porous cermet fuel electrode, and a porous lanthanum manganite air electrode in the form of sintered particles, with solid ceramic oxide electrolyte therebetween, where the air electrode surface next to the electrolyte contains a porous, discontinuous layer of small, discrete cerium oxide particles having diameters from 0.01 micrometer to 0.1 micrometer, and where the electrolyte contacts both the lanthanum manganite and the discontinuous cerium oxide layer.

9. The fuel cell of claim 8, where the electrolyte is stabilized zirconia, the air electrode is from 500 micrometers to 2,000 micrometers thick, 90% to 100% of the cerium oxide particles are in the top 50 micrometers of the air electrode structure next to the electrolyte, and said cerium oxide particles are effective to provide nucleating sites for electrolyte formation.

10. A plurality of the cells of claim 8, electrically connected together.

* * * * *